United States Patent
Giusti et al.

(10) Patent No.: US 7,033,324 B2
(45) Date of Patent: Apr. 25, 2006

(54) APPARATUS FOR TRANSCUTANEOUS BIOPSY OF RIGID TISSUES IN PARTICULAR OSTEOMEDULLARY TISSUE

(75) Inventors: Dario Giusti, Rome (IT); Vito Lelio Burgio, Rome (IT); Gianfranco Casula, Rho (IT)

(73) Assignee: H.S. Hospital Service S.p.A., Pomezia (IT)

( * ) Notice: Subject to any disclaimer, the term of this patent is extended or adjusted under 35 U.S.C. 154(b) by 349 days.

(21) Appl. No.: 10/250,397

(22) PCT Filed: Dec. 21, 2001

(86) PCT No.: PCT/IB01/02618

§ 371 (c)(1),
(2), (4) Date: Jun. 27, 2003

(87) PCT Pub. No.: WO02/053035

PCT Pub. Date: Jul. 11, 2002

(65) Prior Publication Data

US 2004/0059252 A1 Mar. 25, 2004

(30) Foreign Application Priority Data

Dec. 28, 2000 (IT) ......................... MO2000A0288

(51) Int. Cl.
*A61B 10/00* (2006.01)

(52) U.S. Cl. ........................................................ 600/567
(58) Field of Classification Search ................ 600/567, 600/562, 564; 604/170.02, 164.11, 158–169.01, 604/164.02–164.06
See application file for complete search history.

(56) References Cited

U.S. PATENT DOCUMENTS

| 4,785,826 A | 11/1988 | Ward |
| 6,063,037 A | 5/2000 | Mittermeier |
| 6,730,043 B1 * | 5/2004 | Krueger et al. ............. 600/567 |

FOREIGN PATENT DOCUMENTS

| DE | 200 10 879 | 10/2000 |
| WO | WO9627330 | 9/1996 |

* cited by examiner

*Primary Examiner*—Max F. Hindenburg
*Assistant Examiner*—Brian Szmal
(74) *Attorney, Agent, or Firm*—Collard & Roe, P.C.

(57) ABSTRACT

The apparatus (1) for transcutaneous biopsy of rigid tissues includes hollow needle (2) provided with tapered distal end (3), blocking part (10) suitable for being inserted into the hollow needle (2) in order to block a sample of the tissue at the interior of the hollow needle (2), the blocking part (10) includes blade (11;13), handle (6) associated with a proximal end of hollow needle (2), the blocking part (10) is coupled with advancing part (9) suitable for advancing the blocking part (10) inside the hollow needle (2) between a first rear position and a second forward position.

25 Claims, 4 Drawing Sheets

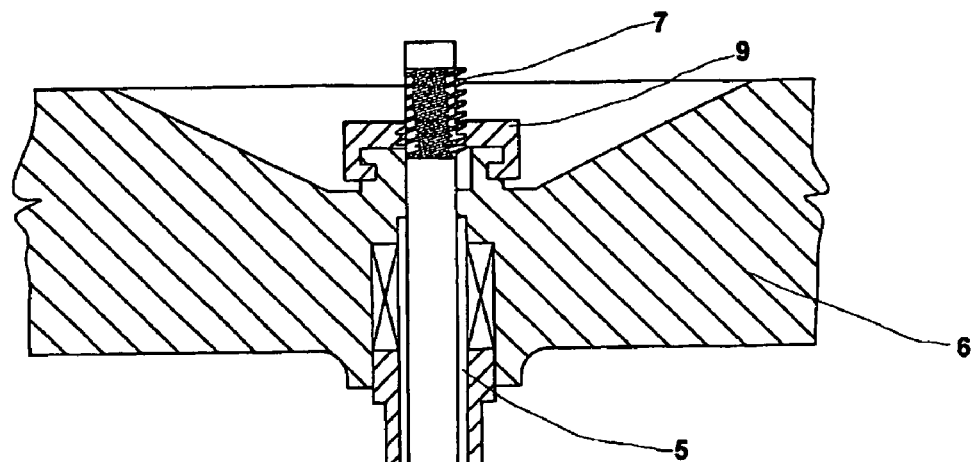
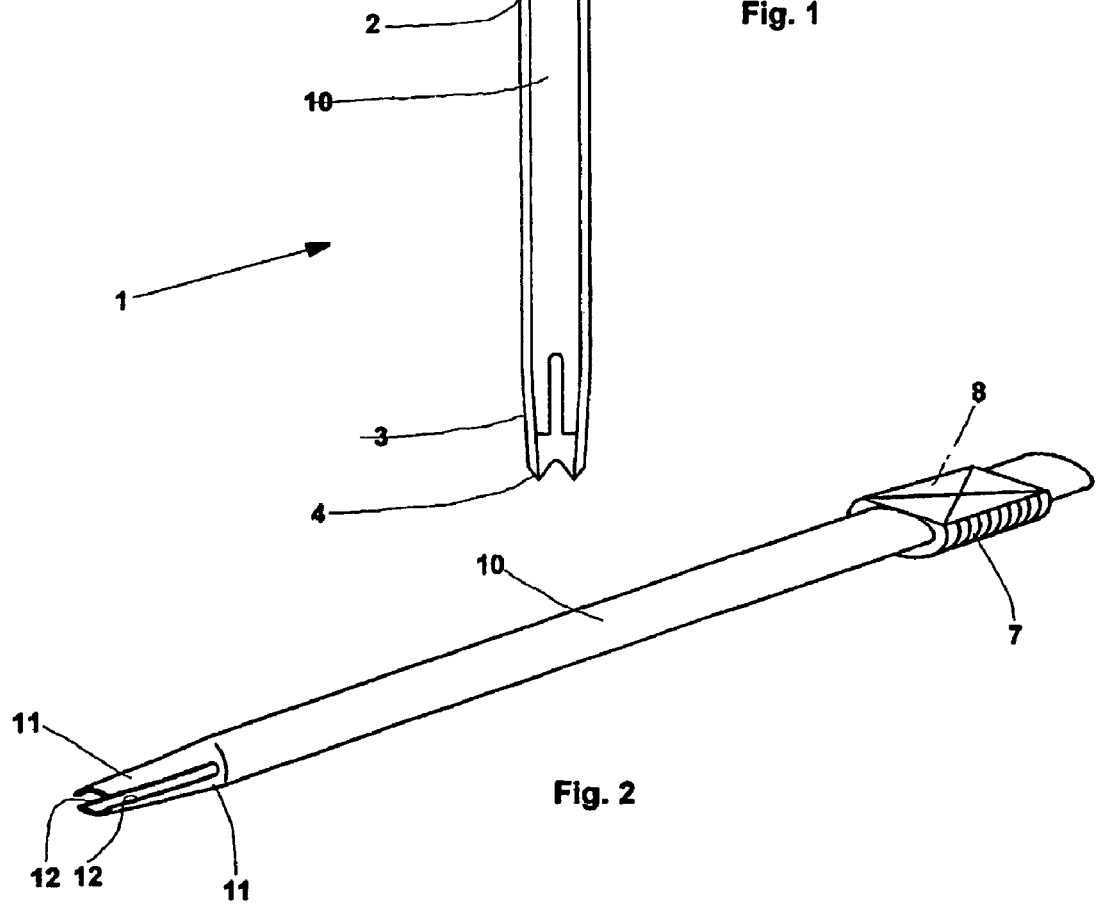
Fig. 1
Fig. 2

APPARATUS FOR TRANSCUTANEOUS BIOPSY OF RIGID TISSUES IN PARTICULAR OSTEOMEDULLARY TISSUE

CROSS REFERENCE TO RELATED APPLICATIONS

Applicants claim priority under 35 U.S.C. §119 of ITALIAN Application No. MO2000A000288 filed on 28 Dec. 2000. Applicants also claim priority under 35 U.S.C. §365 of PCT/IB01/02618 filed on 21 Dec. 2001. The international application under PCT article 21 (2) was published in English.

The present invention relates to an apparatus for transcutaneous biopsy of rigid tissues, in particular osteomedullary tissue, i.e. an apparatus for taking, from the body of a patient, a sample of said tissue, suitable for being submitted to examination.

From the prior art apparatuses are known for transcutaneous biopsy of rigid tissues comprising a needle consisting of a hollow cylinder provided with handle at the proximal end, with the distal end tapered and provided with cutting edge. A hollow, cylindrical rod is suitable for being inserted into the needle, said hollow, cylindrical rod being provided with a small handle at its proximal end and ending, at the distal end, with a curved blade, or a pair of facing, curved blades, separated from each other by a pair of opposed, longitudinal notches.

In order to take from the body of the patient a sample of tissue to be analysed, first of all the needle is inserted into the region of the body of the patient, from which the sample is intended to be taken, the needle being inserted with the aid of a mandrel provided with penetrating tip and suitable for being inserted into the needle. Once the tip of the needle has reached the region from which the sample must be taken, the mandrel is extracted and the needle is further pushed into the tissue. During this manoeuvre, a cylindrical sample of tissue penetrates into the needle, said sample being still connected with the surrounding tissue at one of its own ends. At this point, the aforementioned hollow, cylindrical rod is inserted into the needle and, during such operation, the end of the rod shaped as a blade, or a pair of opposed blades, interposes between the sample of tissue and the internal wall of the needle. If the end of the hollow, cylindrical rod is shaped as a single, curved blade, the tapered tip of the needle causes a deformation of the blade which is deflected towards the axis of the needle and applies a pressure against the sample of tissue, so as to block it by friction on the internal wall of the needle. When the end of the hollow, cylindrical rod is shaped as a pair of opposed blades, the tapered tip of the needle causes a deforms the blades and press them between the internal surface of the needle and the external surface of the sample of tissue, thus causing a coupling by friction between sample of tissue, cylindrical blades and internal surface of the needle, said coupling blocking the sample of tissue at the inside of the needle.

The above mentioned apparatuses show the disadvantage that, during the insertion of the hollow, cylindrical rod, it may be difficult for the end thereof shaped as a blade, or pair of blades, to interpose between the sample of tissue and the internal wall of the needle, with the risk of damaging the sample of tissue, thus making it unusable and making then necessary to take again a sample of tissue, which involves further inconveniences and sufferings for the patient.

In addition, the fact that the hollow, cylindrical rod must be inserted into the needle only after the removal of the mandrel, which is used to facilitate penetration of the needle into the osteomedullary tissue, causes an extension of the times required for taking the sample of tissue and a rising of the risk of incorrect manoeuvres by the person taking the sample.

The present invention intends to provide an apparatus for performing transcutaneous biopsy of rigid tissues, in particular osteomedullary tissue, which does not show the above-mentioned disadvantages.

According to the present invention an apparatus is provided for transcutaneous biopsy of rigid tissues, comprising hollow needle means provided with a tapered distal end, blocking means insertable into said hollow needle means in order to block a sample of said tissue at the inside of said hollow needle, said blocking means comprising cylindrical blade means, handle means associated with a proximal end of said hollow needle, characterised in that, said blocking means is coupled with advancing means suitable for advancing said blocking means into said hollow needle means between a first rear position and a second forward position.

Owing to the invention it is possible to hold the blocking means permanently at the inside of the hollow needle, while the sample is taken, thus reducing the times required for taking the sample. In addition, since the blocking means is permanently inserted at the inside of the hollow needle, there is a remarkable reduction of the risk that the sample of tissue to be taken is damaged by the blade means.

According to another embodiment of the present invention, said blade means comprises a pair of cylindrical opposed blades.

This leads to a more reliable blocking of the sample of tissue to be taken at the inside of the hollow needle.

According to a further embodiment of the present invention, said blade means shows at least an end section inclined towards the axis of said hollow needle, the inclination angle of said end section being smaller than the tapering angle of the distal end of the hollow needle.

This enables the end of said appendix to be placed, at said rear position of the blocking means, at the beginning of the tapering of the distal end of the hollow needle, which makes easier for the sample of tissue to enter into the needle, reduces further the risk that said sample of tissue may be damaged and makes more rapid the advancing manoeuvre of the blocking means from said rear position to said forward position.

The invention will be described here below, with reference to the attached drawings, which illustrate some merely indicative and non-restrictive exemplary embodiments.

FIG. 1 is a longitudinal section of the apparatus according to the invention;

FIG. 2 is a perspective view of the blocking means according to the invention;

Figure 3:
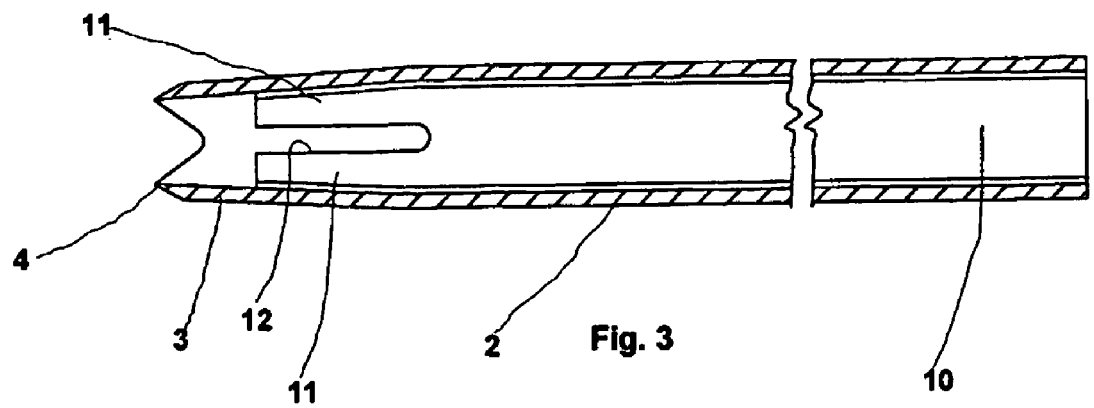
FIG. 3 is a broken, longitudinal section of a detail of FIG. 1, with the blocking means at the rear position inside the hollow needle.
Figure 4:
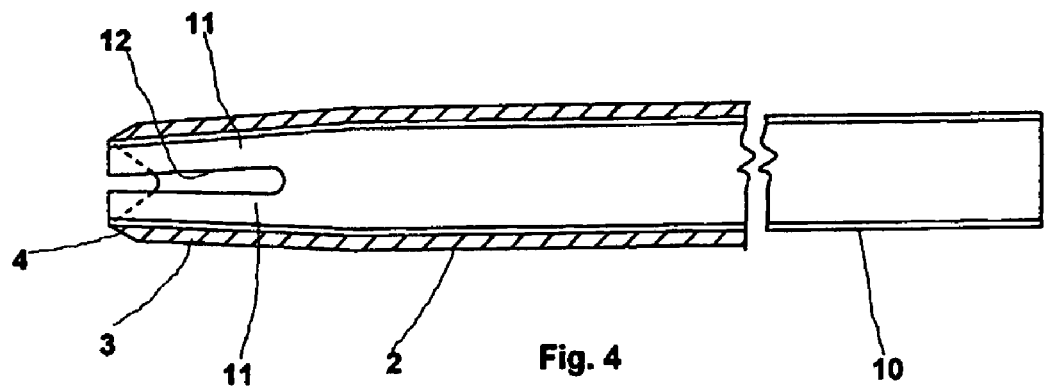
FIG. 4 is a section like FIG. 1, but with the blocking means at the forward position inside the hollow needle.

In FIG. 1, a device 1 is shown according to the invention for transcutaneous biopsy of rigid tissues, comprising a hollow needle 2, ending, at its distal end, with a tapered tip 3, provided with a cutting edge 4, in order to facilitate penetration of the tapered tip 3 into said rigid tissue. The proximal end 5 of the hollow needle 2 is coupled with a handle 6, designed for making easier and safer handling of the hollow needle 2.

A hollow rod 10 is inserted inside the hollow needle 2, said hollow rod having the function of blocking a sample of tissue inside the hollow needle 5. The hollow rod 10 comprises, at its proximal end, a threaded section 7 provided with anti-rotation flattening 8. An internally threaded nut 9 engages the threaded section 7, said nut being coupled with the handle 6 so as to be able to rotate around an axis substantially coincident with the longitudinal axis of the hollow needle 2, without being able of moving along the direction of said axis. By rotating the nut 9 in either direction, the hollow rod 10 moves inside the hollow needle 2 between a rear position and a forward position in a direction parallel to the longitudinal axis of the hollow needle 2. The movement of the hollow rod 10 in said direction is caused by the anti-rotation flattening 8, which prevents the hollow rod 10 from rotating with respect to the hollow needle 2 as a consequence of the rotation of the nut 9.

The hollow rod 10 is provided., at its distal end, with blocking means 11 shaped as a pair of curved blades, separated from each other by a pair of mutually opposed notches 12. The blocking means 11 has the function of blocking inside the hollow needle 2 a sample of tissue penetrated into the needle. The blades 11 may be inclined toward the longitudinal axis of the hollow needle 2, with an inclination angle smaller than the tapering angle of the distal end 3 of the hollow needle 2. When the hollow rod 10 lies at said rear position, the distal end of the blades 11 is positioned at the beginning of the tapered distal end 3 of the hollow needle 2. By advancing the hollow rod 10 inside the hollow needle 2, the blades 11 come into contact with the internal wall of said distal end 3 and are deflected towards the longitudinal axis of the hollow needle 2.

Figure 5:
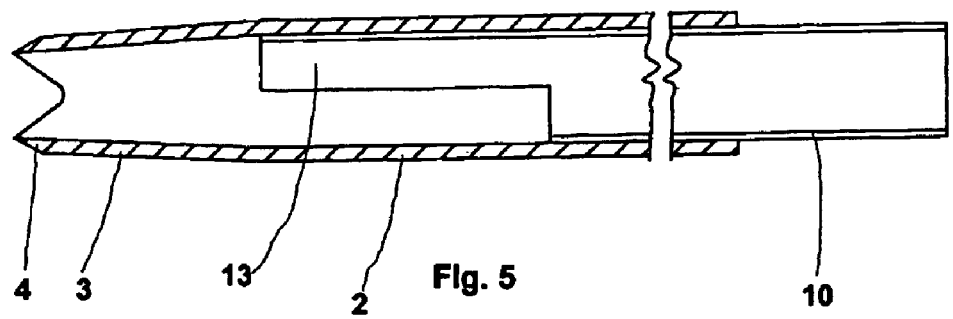
FIGS. 5 and 6 are sections like FIGS. 1 and 2, illustrating a second embodiment of the blocking means.
Figure 6:
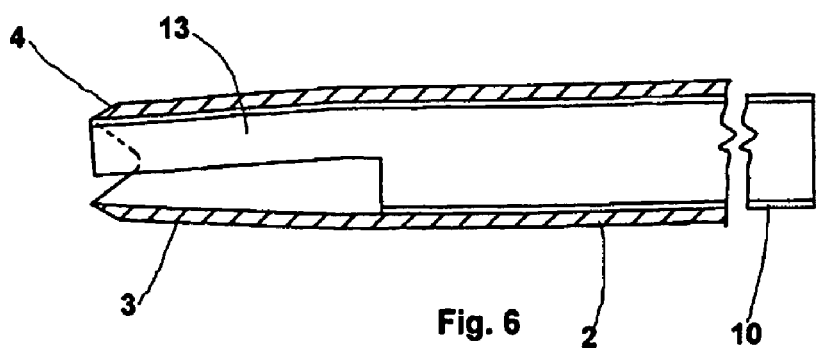
Figure 7:
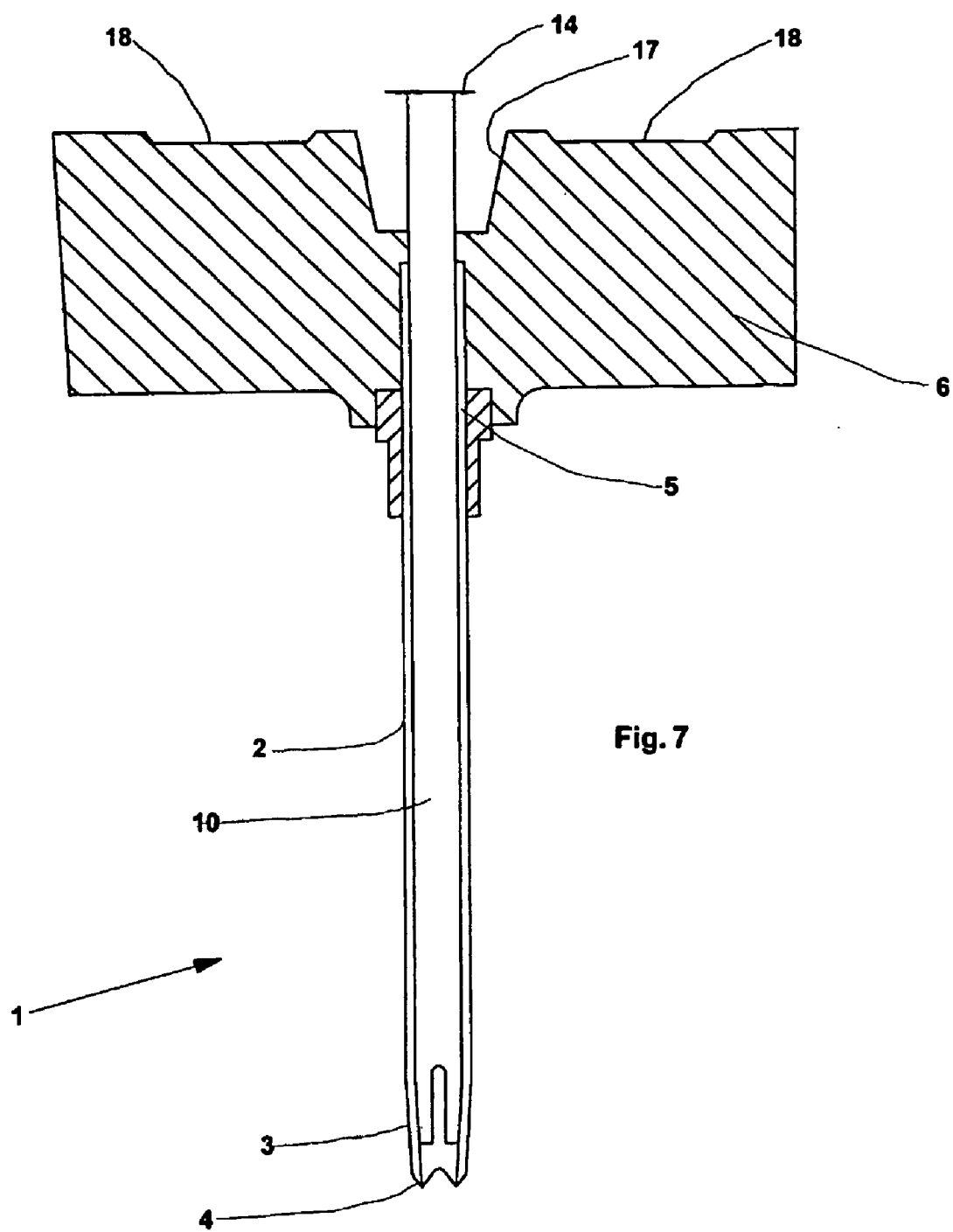
FIG. 7 is a longitudinal section of a variation of the apparatus according to the invention.
Figure 8:
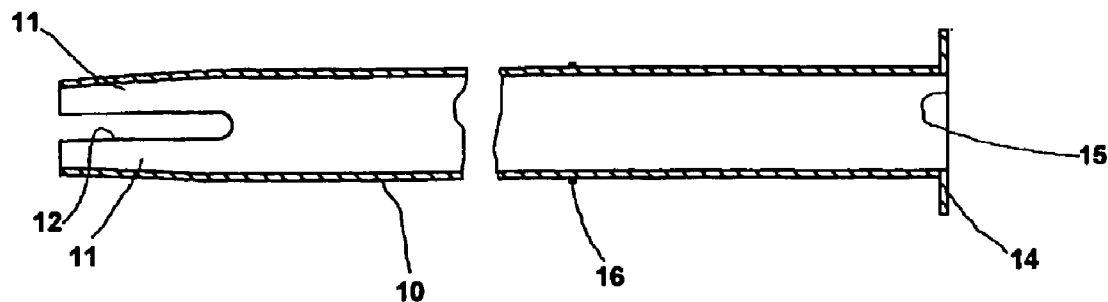
FIG. 8 is a broken longitudinal section of a detail of FIG. 7.
Figure 9:
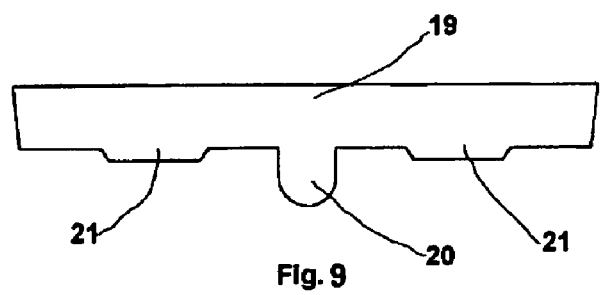
FIG. 9 is a side view of an accessory of the apparatus of FIG. 7.
Figure 10:
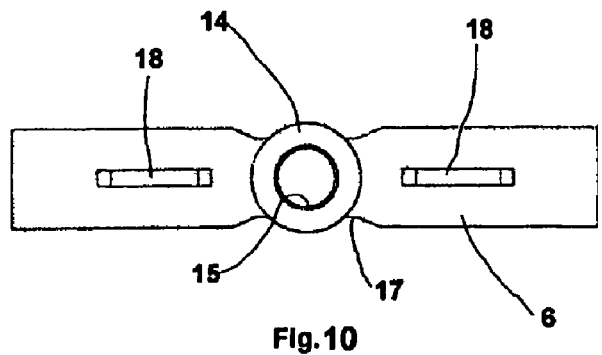
FIG. 10 is a top view of the apparatus of FIG. 7.

In a further version of the invention, shown in FIGS. 5 and 6, the blocking means is shaped as a single curved blade 13 extending, for instance, through an angle of about 180°. When the hollow rod 10 lies at said rear position, the end of said curved blade 13 lies substantially at the beginning of the tapered distal end 3 of the hollow needle 2. By moving the hollow rod 10 from said rear position to said forward position, the curved blade is deflected towards the longitudinal axis of the hollow needle 2, owing to the tapered distal end of the hollow needle 2.

The curved blade 13, at its undeflected position, is substantially parallel to the longitudinal axis of the hollow rod 10. Alternatively, the curved blade 13 may be inclined toward said longitudinal axis, with an inclination angle smaller than the tapering angle of the distal end of the hollow needle 2.

In FIGS. 7 to 10 a variation of the apparatus 1 according to the invention is shown.

In this variation, the hollow rod 10 ends, at its proximal end, with an annular expansion 14, provided with a central bore 15 communicating with the interior of the hollow rod 10. The annular expansion 14 is used for enabling the operator to move the hollow rod 10 between said rear position and said forward position. The handle 6 is provided, at its central region, with a recess 17 suitable for receiving the annular expansion 14, when the hollow rod 10 is advanced from said rear position to said forward position. Two grooves 18 are provided on the upper face of the handle 6 at symmetrical positions with respect to said seat 17, said grooves being suitable for coupling with corresponding ridges 21 of a back portion 19, which may be inserted onto the handle 6 and whose function will be explained here below. The back portion 19 is further provided with central protrusion 20 which may be inserted into the bore 15 of said annular expansion 14.

The hollow rod 10 is provided, at an intermediate position of its length, with an annular seal 16, that, when the hollow rod 10 is inserted into the hollow needle 2, is compressed between the external surface of the hollow rod 10 and the internal surface of the hollow needle 2, thus generating a friction strength sufficient for preventing accidental, unwanted movements of the hollow rod 10 inside the hollow needle 2. The annular seal 16 may be made of rubber-elastic material, for example silicone.

On the external surface of the proximal end of the hollow rod 10 a first reference marker and a second reference marker may be provided, both the markers being suitable for indicating to the user the positioning of the rod 10 at said rear position and at said forward position, respectively.

Working of the apparatus according to the invention, with reference to the embodiment shown in FIGS. 1 to 6, is as follows: when a biopsy of a rigid tissue, for example osteomedullary tissue, is to be performed, it is first of all necessary to insert the hollow needle 2 into the body of the patient, in order to reach the region from which the sample of tissue is to be taken. For this purpose a mandrel, not shown, with a penetration tip is used to facilitate the insertion of the hollow needle 2, not shown, said mandrel being introduced into the hollow rod 10, placed inside the hollow needle 2, until said penetrating tip protrudes from the distal end of the hollow needle 2. Before inserting the hollow needle, the nut 9 is rotated, bringing the hollow rod 10 into its rear position inside the hollow needle 2.

Once the tip 3 of the hollow needle 2 has reached the region of the tissue from which the sample is to be taken, the mandrel is drawn back and the hollow needle 2 is caused to further penetrate into the tissue, so that a sample of the tissue penetrates into the tip 3. This further penetration of the hollow needle 2 is facilitated by the cutting edge 4 of the tip 3.

Once a sample of tissue has penetrated into the tip 3 of the hollow needle 2, the nut 9 is rotated again, to bring the hollow rod 10 from its rear position to its forward position inside the hollow needle 2.

During this manoeuvre, the blocking means 11, 13 comes into contact with the internal wall of the tapered tip 3 of the hollow needle 2 and is deflected towards the longitudinal axis of the hollow needle 2, entrapping the sample of tissue at the interior of said hollow needle 2.

When the blocking means is shaped as a pair of opposed blades 11, the sample of tissue is blocked by being clamped inside the pair of blades 11, owing to deflection of the blades towards the longitudinal axis of the hollow needle 2. When the blocking means is shaped as a single blade 13, the sample of tissue is blocked by friction against the internal wall of the hollow needle 2, because the deflection of the blade 13 towards the longitudinal axis of the needle presses the sample of tissue against said internal wall.

Once the sample of tissue has been blocked inside the hollow needle 2, it is enough to rotate the apparatus 1 in both the directions for separating the sample of tissue from the surrounding tissue.

Once the sample has been taken and the apparatus 1 has been extracted from the body of the patient, the hollow rod 10 is brought back to its rear position, by acting on the manoeuvre nut 9 and then the sample of tissue can be extracted from the needle 2, for example by introducing a pushing element into the needle to push the sample of tissue out of the needle 2, through the tip 3.

When the embodiment of the invention shown in the FIGS. 7 to 10 is used, before introducing the hollow needle 2 into the body of the patient, the operator verifies, by means of said first reference marker, that the hollow rod 10 is placed at said rear position, i.e. with the distal end of the blocking means 11, 13 at the beginning of the tapered end 3 of the hollow needle 2. Subsequently, the operator inserts the mandrel into the hollow rod 10 and introduces the hollow needle 2 into the body of the patient, until it reaches the region from which the sample of tissue is to be taken. When the tip 3 of the hollow needle 2 has reached said region, the mandrel is drawn back and the back portion 19 is placed on the handle 6, by coupling the central protrusion 20 with the bore 15 of the annular expansion 14 and the ridges 19 with the grooves 18 of the handle 6, and the hollow needle 2 is further advanced in order to cause a sample of tissue to penetrate into the tip 3. During this manoeuvre, the back portion 19 protects the annular expansion 14 of the hollow rod 10, preventing said annular expansion 14 from being accidentally pushed down, thus displacing the hollow rod 10 from its rear position.

Finally, the operator removes the back portion 19 and pushes the annular expansion 14, for example by means of the thumb, in order to advance the hollow rod 10 from said rear position to said forward position, at which the blade means 11, 13 blocks the sample of tissue at the interior of the hollow needle 2. The second reference marker is used for indicating to the operator when the hollow rod 10 has reached said forward position.

Lastly, the operator may separate the sample of tissue from the surrounding tissue, extract the needle from the body of the patient and retrieve the sample entrapped at the interior of the hollow needle 2, as before described.

In practice, the materials, the dimensions and the working details may be different from those indicated, but technically equivalent thereto, without departing from the juridical domain of the present invention.

The invention claimed is:

1. Apparatus for transcutaneous biopsy of rigid tissues, comprising
   hollow needle means provided with tapered distal end,
   blocking means suitable for being inserted into said hollow needle means in order to block a sample of tissue at the interior of said hollow needle,
   said blocking means comprising blade means, handle means associated with a proximal end of said hollow needle, said blocking means being coupled with advancing means suitable for advancing said blocking means into said hollow needle means between a first rear position and a second forward position,
   said advancing means comprising threaded nut means suitable for coupling with threaded means provided at a proximal end of said blocking means, wherein said threaded means are provided with an anti-rotation flattening.

2. Apparatus according to claim 1, wherein said threaded nut means is coupled with said handle means in such a way as to be able to rotate around an axis substantially concurrent with the longitudinal axis of said hollow needle means.

3. Apparatus according to claim 2, wherein said threaded nut means is coupled with said handle means in such a way as to be prevented from moving along the direction of said axis.

4. Apparatus according to claim 1, wherein said blocking means comprises a hollow rod.

5. Apparatus according to claim 4, wherein blade means is provided at the distal end of said hollow rod.

6. Apparatus according to claim 5, wherein said blade means comprises a pair of mutually opposed curved blades, separated from each other by a pair of mutually opposed notches.

7. Apparatus according to claim 6, wherein each of said curved blades is inclined towards the longitudinal axis of said hollow needle, with an inclination angle smaller than the tapering angle of said distal end of the hollow needle.

8. Apparatus according to claim 5, wherein said blade means comprises a single curved blade.

9. Apparatus according to claim 8, wherein said single curved blade is inclined towards the longitudinal axis of said hollow needle with an inclination angle smaller than the tapering angle of said distal end of the hollow needle.

10. Apparatus according to claim 4, wherein said hollow rod is provided, at an intermediate position of its length, with annular seal means.

11. Apparatus according to claim 4, wherein said hollow rod is provided, on the external surface of its proximal end, with a first reference marker and a second reference marker, both suitable for indicating, respectively, when said hollow rod lies at said rear position and at said forward position.

12. Apparatus for transcutaneous biopsy of rigid tissues, comprising
    hollow needle means provided with tapered distal end, blocking means suitable for being inserted into said hollow needle means in order to block a sample of tissue at the interior of said hollow needle,
    said blocking means comprising blade means, handle means associated with a proximal end of said hollow needle, said blocking means being coupled with advancing means suitable for advancing said blocking means into said hollow needle means between a first rear position and a second forward position,
    said advancing means comprises pushing means provided at a proximal end of said blocking means,
    wherein said pushing means comprises an annular expansion of the proximal end of said blocking means.

13. Apparatus according to claim 12, wherein said handle means is provided with a central recess suitable for receiving said pushing means when said blocking means, is moved from said rear position to said forward position, and vice versa.

14. Apparatus according to claim 13, wherein said handle means is provided with grooves arranged in substantially symmetrical positions with respect to said central recess.

15. Apparatus according to claim 14, and further comprising handle back portion means suitable for being coupled with said handle means.

16. Apparatus according to claim 15, wherein said handle back portion means is provided with ridges suitable for coupling with said grooves.

17. Apparatus according to claim 15, wherein said handle back portion means is provided with central protrusion suitable for coupling with a central bore of said annular expansion.

18. Apparatus according to claim 12, wherein said blocking means comprises a hollow rod.

19. Apparatus according to claim 18, wherein blade means is provided at the distal end of said hollow rod.

20. Apparatus according to claim 19, wherein said blade means comprises a pair of mutually opposed curved blades, separated from each other by a pair of mutually opposed notches.

21. Apparatus according to claim 20, wherein each of said curved blades is inclined towards the longitudinal axis of said hollow needle, with an inclination angle smaller than the tapering angle of said distal end of the hollow needle.

22. Apparatus according to claim 19, wherein said blade means comprises a single curved blade.

23. Apparatus according to claim 22, wherein said single curved blade is inclined towards the longitudinal axis of said hollow needle with an inclination angle smaller than the tapering angle of said distal end of the hollow needle.

24. Apparatus according to claim 18, wherein said hollow rod is provided, at an intermediate position of its length, with annular seal means.

25. Apparatus according to claim 18, wherein said hollow rod is provided, on the external surface of its proximal end, with a first reference marker and a second reference marker, both suitable for indicating, respectively, when said hollow rod lies at said rear position and at said forward position.

* * * * *